United States Patent
Lee et al.

(10) Patent No.: US 11,690,543 B2
(45) Date of Patent: Jul. 4, 2023

(54) SYSTEM AND METHOD FOR CAMERA-BASED QUANTIFICATION OF BLOOD BIOMARKERS

(71) Applicant: NURALOGIX CORPORATION, Toronto (CA)

(72) Inventors: Kang Lee, Toronto (CA); Andrew Barszczyk, Woodbridge (CA); Sijia Wu, Newmarket (CA); Yousef Yasin, Toronto (CA); Winston De Armas, Toronto (CA); Alan Ding, North Vancouver (CA)

(73) Assignee: NURALOGIX CORPORATION, Toronto (CA)

( * ) Notice: Subject to any disclaimer, the term of this patent is extended or adjusted under 35 U.S.C. 154(b) by 0 days.

(21) Appl. No.: 17/627,297

(22) PCT Filed: Jun. 30, 2020

(86) PCT No.: PCT/CA2020/050912
§ 371 (c)(1),
(2) Date: Jan. 14, 2022

(87) PCT Pub. No.: WO2021/007651
PCT Pub. Date: Jan. 21, 2021

(65) Prior Publication Data
US 2022/0265171 A1    Aug. 25, 2022

Related U.S. Application Data

(60) Provisional application No. 62/874,729, filed on Jul. 16, 2019.

(51) Int. Cl.
*A61B 5/1455* (2006.01)
*G06N 20/20* (2019.01)
(Continued)

(52) U.S. Cl.
CPC ........ *A61B 5/1455* (2013.01); *A61B 5/14532* (2013.01); *A61B 5/14551* (2013.01); *G06N 20/10* (2019.01); *G06N 20/20* (2019.01)

(58) Field of Classification Search
CPC .............. A61B 5/1455; A61B 5/14551; A61B 5/14532; A61B 5/0205; A61B 5/0075; G06N 20/10; G06N 20/20
See application file for complete search history.

(56) References Cited

U.S. PATENT DOCUMENTS

| 9,535,053 B1 * | 1/2017 | Cafferty ................... G01J 3/28 |
| 2007/0015971 A1 * | 1/2007 | Atignal .................... A61B 5/00 |
| | | 600/300 |

(Continued)

FOREIGN PATENT DOCUMENTS

| CN | 108697386 A | 10/2018 |
| CN | 109937002 A | 6/2019 |
| JP | 2012152556 A | 8/2012 |

OTHER PUBLICATIONS

International Search Report of the International Searching Authority for application No. PCT/CA2020/050912 dated Jun. 30, 2020.

(Continued)

*Primary Examiner* — Chu Chuan Liu
(74) *Attorney, Agent, or Firm* — Bhole IP Law; Anil Bhole; Marc Lampert

(57) ABSTRACT

Provided are systems and methods for determination of a concentration of one or more blood biomarkers of a human subject. The method including: determining, using a first machine learning model trained with a hemoglobin concentration (HC) changes training set, bit values from a set of bitplanes in a captured image sequence that represent the HC changes of the subject, the set of bitplanes being those that are determined to approximately maximize a signal-to-noise ratio (SNR), the HC changes training set including bit values (Continued)

from each bitplane of images captured from a set of subjects for which HC changes are known; determining, using a second machine learning model trained using a blood biomarkers training set, concentration of one or more blood biomarkers, the blood biomarkers training set including previously determined HC change signals from other subjects and one or more blood panels from those subjects as ground truth data.

18 Claims, 14 Drawing Sheets

(51) Int. Cl.
*G06N 20/10* (2019.01)
*A61B 5/145* (2006.01)

(56) References Cited

U.S. PATENT DOCUMENTS

| 2015/0141778 | A1 | 5/2015 | Segman |
| 2016/0098592 | A1* | 4/2016 | Lee ..................... G06K 9/6278 434/236 |
| 2018/0199870 | A1 | 7/2018 | Lee et al. |
| 2019/0008392 | A1* | 1/2019 | Wang ................. A61B 5/14551 |

OTHER PUBLICATIONS

Written Opinion of the International Searching Authority for application No. PCT/CA2020/050912 dated Jun. 30, 2020.
First Office Action for Japanese patent application No. 2022-502880; dated Nov. 18, 2022.
First Office Action for Chinese patent application No. 2020800650499; dated Oct. 28, 2022.

* cited by examiner

SYSTEM AND METHOD FOR CAMERA-BASED QUANTIFICATION OF BLOOD BIOMARKERS

TECHNICAL FIELD

The following relates generally to detection of blood biomarkers and more specifically to a system and method for camera-based quantification of blood biomarkers.

BACKGROUND

A blood panel is a scientific analysis of a blood sample. The sample is typically collected by a trained professional from a vein using a hypodermic needle, or from a finger prick. The panel is typically a collection of tests for precisely quantifying specific blood components. Blood panels are a crucial tool in health care for determining physiological and biochemical states, such as disease, mineral content, pharmaceutical drug effectiveness, organ function, among others. Blood panels are usually expensive, invasive and uncomfortable, which limits their use for frequent monitoring applications. Further, such panels may require several days to obtain results.

SUMMARY

In an aspect, there is provided a method for determination of a concentration of one or more blood biomarkers of a human subject, the method comprising: receiving a captured image sequence of light re-emitted from the skin of the human subject; determining, using a first machine learning model trained with a hemoglobin concentration (HC) changes training set, bit values from a set of bitplanes in the captured image sequence that represent the HC changes of the subject, the set of bitplanes being those that are determined to approximately maximize a signal-to-noise ratio (SNR), the HC changes training set comprising bit values from each bitplane of images captured from a set of subjects for which HC changes are known; determining, using a second machine learning model trained using a blood biomarkers training set, concentration of one or more blood biomarkers, the blood biomarkers training set comprising previously determined HC change signals from other subjects and one or more blood panels from those subjects as ground truth data; and outputting the determined concentration of one or more blood biomarkers.

In a particular case of the method, determining the bit values comprises determining a bit values for each of a plurality of predetermined regions of interest (ROIs) of the human subject captured by the images based on the HC changes.

In another case of the method, the ROIs are non-overlapping.

In yet another case of the method, the concentration of one or more blood biomarkers determined using the second machine learning model comprises an estimated statistical probability that a blood concentration of each of the one or more blood biomarkers belongs to a particular concentration range.

In yet another case of the method, the concentration ranges are associated with clinically significant concentration classes.

In yet another case of the method, the captured image sequence comprises images captured in a moving time window, and wherein the determined concentration of one or more blood biomarkers is outputted for each moving time window.

In yet another case of the method, each of the one or more blood biomarkers comprise one of blood glucose concentration, fasting blood glucose, hemoglobin A1c, high density lipoprotein, low density lipoprotein, triglycerides, neutrophils, basophils, creatinine, uric acid, red blood cells, hemoglobin, platelets, sediment, and albumin.

In yet another case of the method, determining a set of bitplanes that maximize SNR comprises: performing pixel-wise image subtraction and addition of bitplane vectors to maximize signal differences in all ROIs over a predetermined time period; identifying bit values from bitplanes that increase the signal differentiation and bit values from bitplanes that decrease the signal differentiation or do not contribute to signal differentiation; and discarding the bit values from the bitplanes that decrease the signal differentiation or do not contribute to signal differentiation.

In yet another case of the method, the second machine learning model comprises a Long Short Term Memory (LSTM) artificial neural network or Gaussian Process Inference Networks (GPNet).

In another aspect, there is provided a system for determination of a concentration of one or more blood biomarkers of a human subject, the system comprising one or more processors and a data storage device, the one or more processors configured to execute: a TOI module to receive a captured image sequence of light re-emitted from the skin of the human subject and to determine, using a first machine learning model trained with a hemoglobin concentration (HC) changes training set, bit values from a set of bitplanes in the captured image sequence that represent the HC changes of the subject, the set of bitplanes being those that are determined to approximately maximize a signal-to-noise ratio (SNR), the HC changes training set comprising bit values from each bitplane of images captured from a set of subjects for which HC changes are known; a quantification module to determine, using a second machine learning model trained using a blood biomarkers training set, concentration of one or more blood biomarkers, the blood biomarkers training set comprising previously determined HC change signals from other subjects and one or more blood panels from those subjects as ground truth data; and an output module to output the determined concentration of one or more blood biomarkers.

In a particular case of the system, determining the bit values comprises determining a bit values for each of a plurality of predetermined regions of interest (ROIs) of the human subject captured by the images based on the HC changes.

In another case of the system, the ROIs are non-overlapping.

In yet another case of the system, the concentration of one or more blood biomarkers determined using the second machine learning model comprises an estimated statistical probability that a blood concentration of each of the one or more blood biomarkers belongs to a particular concentration range.

In yet another case of the system, the concentration ranges are associated with clinically significant concentration classes.

In yet another case of the system, the captured image sequence comprises images captured in a moving time window, and wherein the determined concentration of one or more blood biomarkers is outputted for each moving time window.

In yet another case of the system, each of the one or more blood biomarkers comprise one of blood glucose concentration, fasting blood glucose, hemoglobin A1c, high density lipoprotein, low density lipoprotein, triglycerides, neutrophils, basophils, creatinine, uric acid, red blood cells, hemoglobin, platelets, sediment, and albumin.

In yet another case of the system, determining a set of bitplanes that maximize SNR comprises: performing pixel-wise image subtraction and addition of bitplane vectors to maximize signal differences in all ROIs over a predetermined time period; identifying bit values from bitplanes that increase the signal differentiation and bit values from bitplanes that decrease the signal differentiation or do not contribute to signal differentiation; and discarding the bit values from the bitplanes that decrease the signal differentiation or do not contribute to signal differentiation.

In yet another case of the system, the second machine learning model comprises a Long Short Term Memory (LSTM) artificial neural network or Gaussian Process Inference Networks (GPNet).

These and other aspects are contemplated and described herein. It will be appreciated that the foregoing summary sets out representative aspects of embodiments to assist skilled readers in understanding the following detailed description.

BRIEF DESCRIPTION OF THE DRAWINGS

The features of the invention will become more apparent in the following detailed description in which reference is made to the appended drawings wherein.

DETAILED DESCRIPTION

Figure 1:
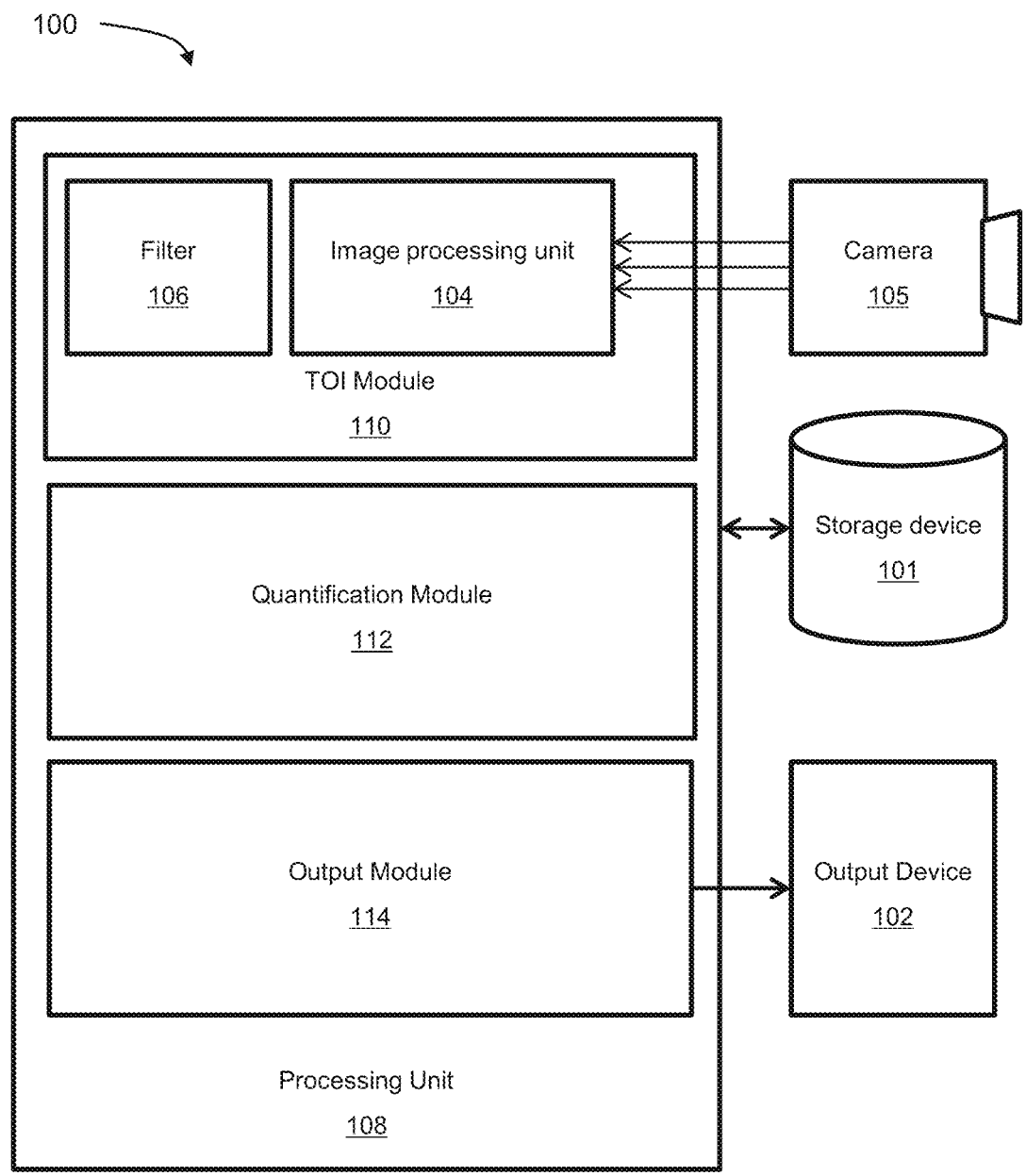
FIG. 1 is a block diagram of a system for camera-based quantification of blood biomarkers, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to detection of blood determinations and more specifically to a system and method for camera-based quantification of blood biomarkers.

In embodiments described herein, the camera-based quantification of blood biomarkers is retrieved from video captured of a human subject's face. The blood biomarkers can include, for example, detection of the concentration of blood glucose, fasting blood glucose, hemoglobin A1c, cholesterols (e.g., high density lipoprotein, low density lipoprotein), triglycerides, immune cells (e.g., neutrophils, basophils), metabolites (e.g., creatinine, uric acid), blood components and proteins (e.g., red blood cells, hemoglobin, platelets, and sediment), albumin, and other contents in the blood. Advantageously, the present embodiments provide a remote and non-invasive approach by which to quantify blood biomarkers with a relatively high-degree of confidence.

Measuring blood biomarkers using hemoglobin concentration changes, in accordance with the embodiments described herein, offers substantial advantages over invasive blood testing approaches. It can be done frequently and quickly because it can be done comfortably and non-invasively anywhere, for example, with just a mobile device. It is inexpensive because it does not require a lab for collecting and processing blood samples. Thus, using the embodiments described herein, more frequent monitoring of blood biomarkers can be performed, increasing the likelihood that abnormal concentrations of blood biomarkers can be detected and acted upon early. Such action may include making lifestyle changes (e.g., diet or otherwise), and/or following up with more comprehensive bloodwork analysis and medical advice. More frequent testing can also provide a more comprehensive picture of a person's health.

Some approaches to blood tests can achieve results with less blood, less expense, and less waiting by miniaturizing assays onto a chip using microfluidics and developing new biomarkers for more efficient testing. However, such approaches still require harvesting blood, and specialized equipment or laboratory techniques to analyze blood samples. There have been attempts to find approaches that do not require the taking of blood. For example, one approach can determine potassium concentration in the blood by using machine learning to detect subtle changes in an Electrocardiogram (ECG). The disadvantage is that such a test still requires specialized equipment; for example the ECG.

In an approach, video-based photoplethysmography can be used. In remote video photoplethysmography, ambient light passes through the skin and into superficial blood vessels. Specific wavelengths of light are absorbed by hemoglobin in the blood as its concentration oscillates with the cardiac cycle. This absorbed light is not reflected back out of the skin and to the camera. These subtle attenuations of light are detected by the camera and represent blood flow. Advantageously, blood flow patterns obtained via video-based photoplethysmography can contain information predictive of the concentration of various blood biomarkers. In particular, blood flow patterns can estimate blood glucose, fasting blood glucose, hemoglobin A1c, cholesterols (e.g., high density lipoprotein, low density lipoprotein), triglycerides, immune cells (e.g., neutrophils, basophils), metabolites (e.g., creatinine, uric acid, albumin), blood components and proteins (e.g., red blood cells, hemoglobin, platelets, and sediment), albumin, and other contents in the blood to varying degrees. However, other approaches to video-based photoplethysmography generally lack robustness required to quantify blood biomarkers with relatively a high degree of precision and accuracy.

The sympathetic and parasympathetic nervous systems or the hormonal control of the cardiovascular system by the renin-angiotensin-aldosterone system are responsive to the concentration of blood biomarkers. It has been found that an individual's blood flow is controlled by the sympathetic and parasympathetic nervous system and the renin-angiotensin-aldosterone system, which is beyond the conscious control of the vast majority of individuals. Individuals' concentration of blood biomarkers can be detected by monitoring their blood flow. The concentration of various contents of the blood, or other biological processes that affect the concentration of blood biomarkers, affect an individual's cardiovascular physiology by adjusting activations of the sympathetic and parasympathetic nervous system, or by causing the release of hormones into the bloodstream by the renin-angiotensin-aldosterone system. The sympathetic nervous system is associated with a quick onset of fight or flight physiology, and the parasympathetic nervous system is associated with resting physiology. The renin-angiotensin-aldosterone system is involved in slow onset, long lasting responses in heart rate and vascular tone. Other factors may also influence blood flow (for example, blood volume, blood density, blood vessel inflammation, blood vessel wall properties, and the like), and such factors could be associated with concentrations of blood biomarkers.

Blood flow in most parts of the face, for example eyelids, cheeks and chin, is predominantly controlled by the sympathetic vasodilator neurons, whereas blood flowing in other areas, for example nose and ears, is mainly controlled by the sympathetic vasoconstrictor neurons. In other areas, for example the forehead region, the blood flow is innervated by both sympathetic and parasympathetic vasodilators. Global changes in the cardiovascular system are generally controlled by the renin-angiotensin-aldosterone system. As concentrations of blood biomarkers fluctuate, they elicit differential spatial and temporal activation patterns on the different parts of the face, as well as globally throughout all blood vessels. In the present embodiments, facial hemoglobin concentration (HC) changes in various facial areas can be extracted to determine information about the state of the autonomic nervous system, the renin-angiotensin-aldosterone system, or another determinant of blood flow. These multidimensional and dynamic arrays of data from an individual area can be compared to models based on normative data, as described herein. From such comparisons, the present embodiments can be used to make reliable statistically based estimations about the concentration of an individual's blood biomarkers.

Referring now to FIG. 1, a system for camera-based quantification of blood biomarkers 100 is shown. The system 100 includes a processing unit 108, one or more video-cameras 105, a storage device 101, and an output device 102. The processing unit 108 may be communicatively linked to the storage device 101 which may be preloaded and/or periodically loaded with video imaging data obtained from one or more video-cameras 105. The processing unit 108 includes various interconnected elements and modules, including a TOI module 110, a quantification module 112, and an output module 114. The TOI module includes an image processing unit 104 and a filter 106. The video images captured by the video-camera 105 can be processed by the filter 106 and stored on the storage device 101. In further embodiments, one or more of the modules can be executed on separate processing units or devices, including the video-camera 105 or output device 102. In further embodiments, some of the features of the modules may be combined or run on other modules as required.

The term "video", as used herein, can include sets of still images. Thus, "camera" can include a camera that captures a sequence of still images that form a video.

Figure 3:
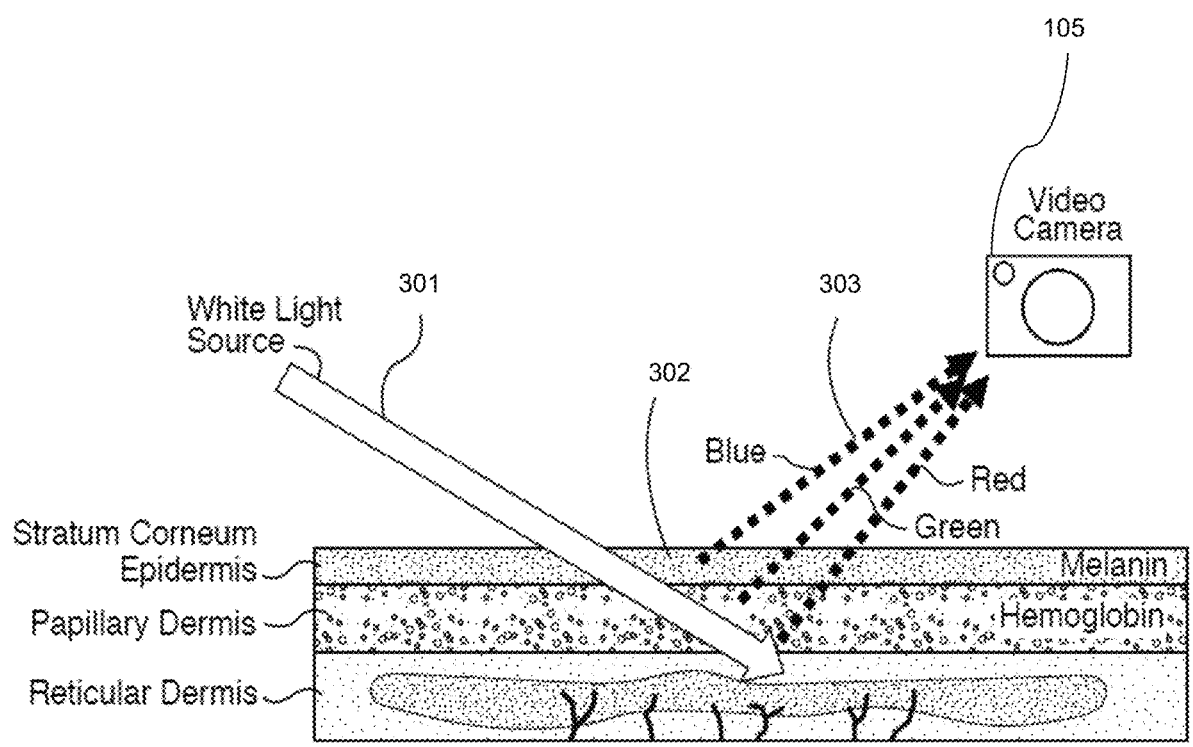
FIG. 3 illustrates re-emission of light from skin epidermal and subdermal layers.
Figure 4:
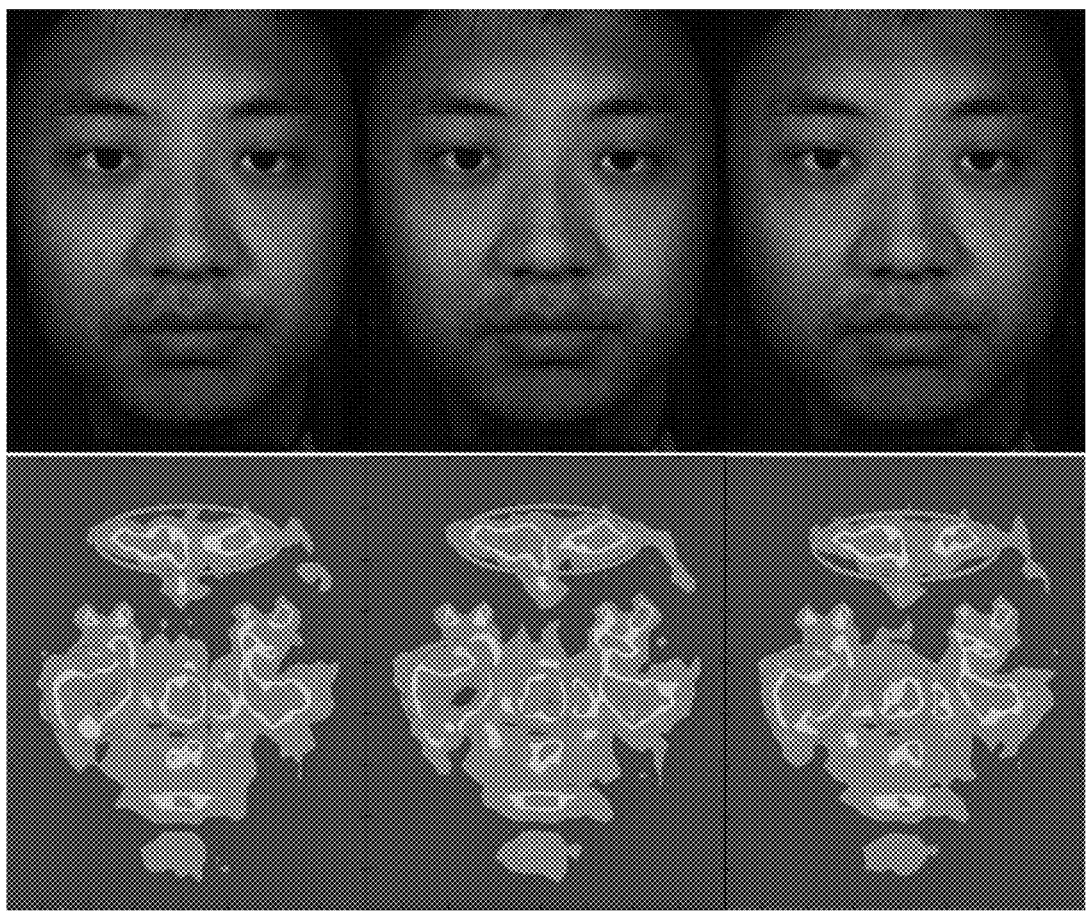
FIG. 4 is a set of surface and corresponding transdermal images illustrating change in hemoglobin concentration for a particular human subject at a particular point in time.

Using transdermal optical imaging (TOI), the TOI module 110 can isolate hemoglobin concentration (HC) from raw images taken from a traditional digital camera, and the quantification module 112 can correlate spatial-temporal changes in HC to the concentration of blood biomarkers. Referring now to FIG. 3, a diagram illustrating the re-emission of light from skin is shown. Light 301 travels beneath the skin 302, and re-emits 303 after travelling through different skin tissues. The re-emitted light 303 may then be captured by optical cameras 105. The dominant chromophores affecting the re-emitted light are melanin and hemoglobin. Since melanin and hemoglobin have different color signatures, it has been found that it is possible to obtain images mainly reflecting HC under the epidermis as shown in FIG. 4.

Using transdermal optical imaging (TOI), the TOI module 110, via the image processing unit 104, obtains each captured image or video stream, from the camera 105, and performs operations upon the image to generate a corresponding optimized hemoglobin concentration (HC) image of the subject. From the HC data, the facial blood flow localized volume concentrations can be determined; whereby localized volume concentrations refer to measured HC intensity values within a region of interest. As described, regions of interest are used to define a localized bounded area, or areas, for which HC is to be measured. The image processing unit 104 isolates HC in the captured video sequence. In an exemplary embodiment, the images of the subject's faces are taken at 30 frames per second using a digital camera 105. It will be appreciated that this process may be performed with alternative digital cameras, lighting conditions, and frame rates.

The TOI module 110 can use the first machine learning model to determine HC by analyzing bitplanes in the video sequence to determine and isolate a set of the bitplanes that approximately maximize the signal to noise ratio (SNR) and, therefore, optimize signal differentiation between different concentrations of blood biomarkers on the facial epidermis (or any part of the human epidermis). In most cases, SNR is a ratio of energy in the heart rate frequency band to energy outside of the heart rate frequency band. Whereby the heart rate frequency band is the range of frequencies that encompasses human heart rate. The determination of high SNR bitplanes is made with reference to an HC training set of images constituting the captured video sequence, in some cases, supplied along with EKG, pneumatic respiration, blood pressure, laser Doppler data collected from the human subjects from which the training set is obtained. In some cases, the EKG and pneumatic respiration data may be used to remove cardiac, respiratory, and blood pressure data in the HC data to prevent such activities from masking the more-subtle blood biomarkers-related signals in the HC data. In the present embodiments, the TOI module 110 trains a first machine learning model for estimating concentrations of blood biomarkers using spatial-temporal signal patterns of epidermal HC changes in regions of interest ("ROIs) extracted from the optimized "bitplaned" images of a sample of human subjects. In some cases, the regions of interest (ROIs) are of a human subject's face; for example, forehead, nose, and cheeks, may be defined as stationary or dynamically updated using the video images. In some cases, the ROIs are non-overlapping. In some cases, the ROIs are selected on the basis of knowledge in the art in respect of ROIs for which HC is particularly indicative of estimating blood biomarkers (for example, forehead, cheek, or the like). Using native images that consist of the bitplanes (typically 24 bitplanes for each color image), signals that change over a particular time period (for example, 10 seconds) on each of the ROIs are extracted. In some cases, the dynamically updated ROIs can be chosen and/or maintained by using face-tracking techniques.

Figure 6:
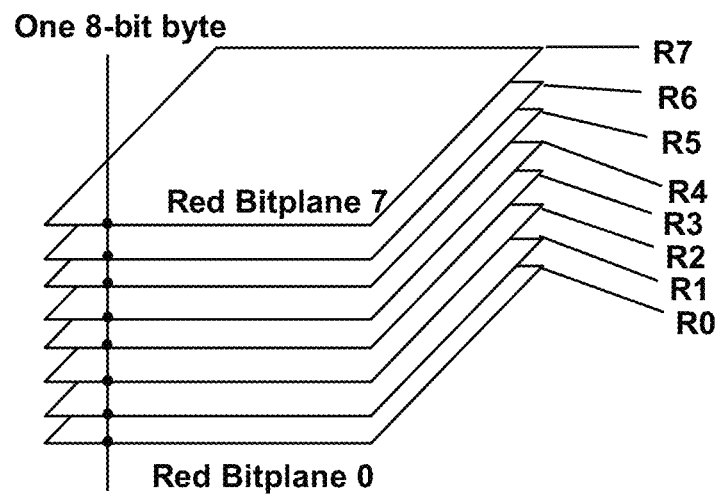
FIG. 6 is an example illustration of bitplanes for a three channel image.
Figure 6:
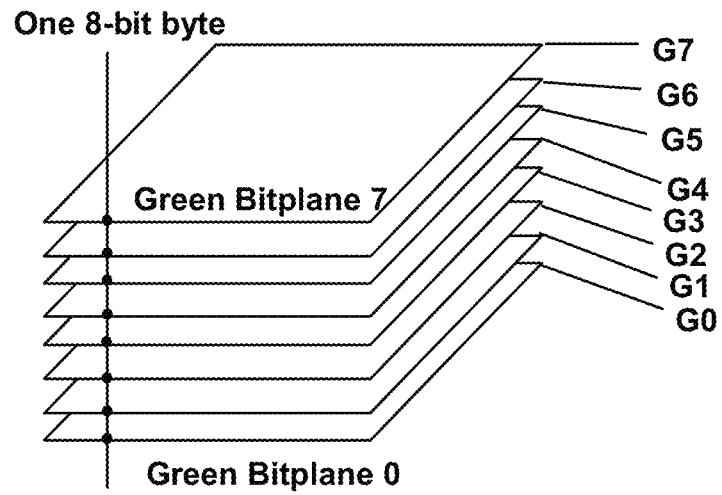
Figure 6:
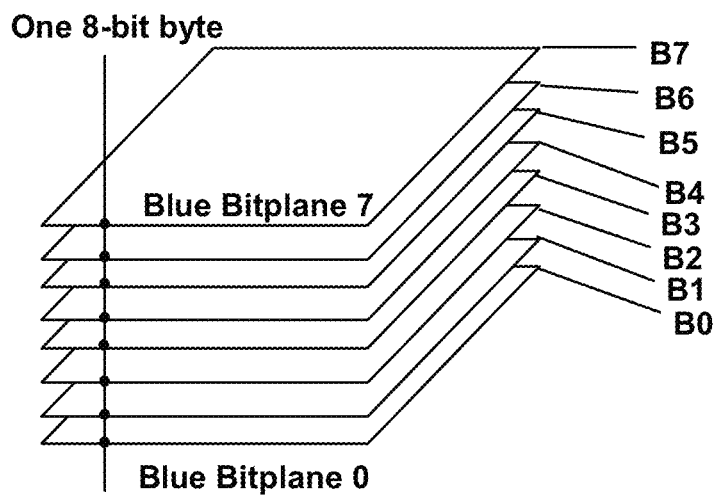

Bitplanes are a fundamental aspect of digital images. Typically, a digital image consists of certain number of pixels (for example, a width×height of 1920×1080 pixels). Each pixel of the digital image having one or more channels (for example, color channels red, green, and blue (RGB)). Each channel having a dynamic range, typically 8 bits per pixel per channel, but occasionally 10 bits per pixel per channel for high dynamic range images. Whereby, an array of such bits makes up what is known as the bitplane. In an example, for each image of color videos, there can be three channels (for example, red, green, and blue (RGB)) with 8 bits per channel. Thus, for each pixel of a color image, there are typically 24 layers with 1 bit per layer. A bitplane in such a case is a view of a single 1-bit map of a particular layer of the image across all pixels. For this type of color image, there are therefore typically 24 bitplanes (i.e., a 1-bit image per plane). Hence, for a 1-second color video with 30 frames per second, there are at least 720 (30×24) bitplanes. FIG. 6 is an exemplary illustration of bitplanes for a three-channel image (an image having red, green and blue (RGB) channels). Each stack of layers is multiplied for each channel of the image; for example, as illustrated, there is a stack of bitplanes for each channel in an RGB image. In the embodiments described herein, Applicant recognized the advantages of using bit values for the bitplanes rather than using, for example, merely the averaged values for each channel. Thus, a greater level of accuracy can be achieved for making predictions of HC changes, and thus blood content quantification as disclosed herein. Particularly, a greater accuracy is possible because employing bitplanes provides a greater data basis for training the machine learning model.

As described herein, blood biomarkers can be determined from the blood flow signal obtained using bitplane analysis. Bitplane analysis can ensure that the signal captured is almost exclusively blood flow information (high signal-to-noise ratio), and that it is not unduly influenced by non-blood flow factors like skin melanin content (e.g., from skin color differences) and light conditions. Generally, changes in blood flow resulting from changes in blood biomarkers can be very subtle; and thus, advantageously, using bitplane analysis as in the present embodiments offers a robust, precise, and reliable way of extracting a blood flow signal, which is generally needed to make accurate predictions of blood biomarkers.

In some cases, raw signals from the camera can be pre-processed using one or more filters 106, depending on the signal characteristics. Such filters 106 may include, for example, a Butterworth filter, a Chebycheff filter, or the like. Using the filtered signals from two or more ROIs, the TOI module 110 can use the first machine learning model to systematically identify bitplanes that will significantly increase the signal differentiation (for example, where the SNR improvement is greater than 0.1 db) and bitplanes that will contribute nothing or decrease the signal differentiation.

After discarding the latter, the remaining bitplanes can be used by the quantification module 112 to estimate blood content concentrations.

For passing to the first machine learning model, the TOI module 110 can first manipulate the bitplane vectors (for example, 24 bitplanes×60 hz) using the bit value in each pixel of each bitplane along the temporal dimension. In one embodiment, this can involve subtraction and addition of each bitplane to maximize the signal differences in ROIs over the time period. In some cases, the addition or subtraction can be performed in a pixelwise manner. In some cases, to obtain reliable and robust machine learning models, the training data for the first machine learning model can be divided into three sets: a training set (for example, 80% of the whole subject data), a test set (for example, 10% of the whole subject data), and an external validation set (for example, 10% of the whole subject data). Generally, the time period of the training data can vary depending on the length of the raw data (for example, 15 seconds, 60 seconds, or 120 seconds). The first machine learning model can use any suitable machine learning technique; for example, using a Long Short Term Memory (LSTM) neural network, Gaussian Process Inference Networks (GPNet), or other types of Artificial Neural Networks (ANN). The machine learning technique for the first machine learning model can be selected based on accuracy and efficiency in, for example, determining improvement of differentiation in terms of accuracy, which bitplane(s) contributes the best information, and which bitplane(s) does not in terms of feature selection.

In an embodiment using the Long Short Term Memory (LSTM) neural network, the TOI module 110 can perform group feature selections and classifications. In this way, the TOI module 110 can obtain a set of bitplanes to be isolated from image sequences to reflect temporal changes in HC. In some cases, the TOI module 110 can use an image filter to isolate the identified bitplanes, as described herein. In this way, the first machine learning model can be used to assess the existence of common spatial-temporal patterns of hemoglobin changes across subjects (for example, differences in amplitude in blood flow changes in the forehead and the cheek over time).

To extract facial blood content quantities, the quantification module 112 can estimate blood content quantities by passing the facial HC change data, from the TOI module 110, to a second machine learning model. In some cases, the facial HC change data can include each pixel of each subject's face image as a function of time. In some cases, to increase signal-to-noise ratio (SNR), the subject's face can be divided into a plurality of regions of interest (ROIs), as described herein, and the data in each ROI can be averaged.

In an embodiment, for obtaining training data for training of the second machine learning model, video images of test subjects are captured and a blood panel of each subject is obtained; the blood panel comprising concentrations of one or more blood biomarkers. This blood panel may include, for example, the concentration of blood glucose, fasting blood glucose, hemoglobin A1c, cholesterols (e.g., high density lipoprotein, low density lipoprotein), triglycerides, immune cells (e.g., neutrophils, basophils), metabolites (e.g., creatinine, uric acid), blood components and proteins (e.g., red blood cells, hemoglobin, platelets, and sediment), albumin, and other blood biomarkers. Subjects may comprise healthy individuals or individuals with suspected abnormalities. In some cases, the training data for the first machine learning model can be obtained at the same time as the training data for the second machine learning model. In such cases, corollary input data of the subjects may be obtained from the collection of the physiological data, for example, to help normalize for physiological effects that are not related to the concentrations of blood biomarkers. Such physiological data can include, for example, EKG, pneumatic respiratory, blood pressure, and laser Doppler which can be collected using an EKG machine, a pneumatic respiration machine, a continuous blood pressure machine, and a laser Doppler machine, or the like. The corollary data can provide additional information for training of the second machine learning model.

The second machine learning model can use any suitable deep learning approach; for example, a Long Short Term Memory (LSTM) neural network, Gaussian Process Inference Networks (GPNet), or other types of Artificial Neural Networks (ANN). In some cases, the second machine learning model can be trained from a portion of the training data, which can be tested using other portions representing a test data set and externally validated using other portions representing an external validation data set. In further cases, classical supervised machine learning techniques may also be used; for example, tree-based models (for example, Random Forest models, and the like), gradient-boosting methods (for example, XGBoost, and the like), and support vector machines. In further cases, unsupervised clustering techniques can be used; for example, t-Distributed Stochastic Neighbor Embedding, or t-SNE.

Once the second machine learning model is trained, the quantification module 112 can obtain a video sequence of any subject and apply the HC extracted from selected bitplanes to the second machine learning model to estimate a concentration range for each of one or more blood biomarkers. In some cases, the output of the second machine learning model can be an estimated statistical probability that the subject's blood concentration of a given blood biomarker belongs to a specific concentration range from the reference blood sample. In such cases, reference blood biomarker concentrations can be obtained via blood panels and then segmented into "classes"; for example, blood glucose 0 to 3 mmol/L is Class 1, blood glucose 3 to 6 mmol/L is Class 2, and so on. The second machine learning model can be trained, using these reference blood biomarker concentrations, to predict a concentration "class" for a particular blood biomarker (output) from the features of a concurrently obtained blood flow signal (inputs). In some cases, the range of each concentration class can be selected based on how well the features of a given blood flow signal can differentiate between one concentration class and another in a predictive model. The range should generally be sufficiently large as to attain a minimum average classification accuracy (% specificity, % sensitivity) across the model as a whole. In other cases, ranges could correspond to clinically significant concentration classes (for example, for blood glucose concentration, Low/Hypoglycemia: <4 mmol/L, Normal: 4-6.9 mmol/L, Elevated: 7-10.9 mmol/L, and High/Diabetes: ≥11 mmol/L), or be determined randomly or arbitrarily. In some cases, for long running video streams when concentrations of blood components fluctuate, changes of the class and probability estimation over time relying on HC data based on a moving time window (for example, 10 seconds) may be used.

In some cases, when making predictions using the second machine learning model, the quantification module 112 can determine the statistical probability that a given blood flow pattern belongs to each concentration class; for example, using a Softmax function as described herein. In an example, this could produce probabilities of 0.06, 0.64, 0.20, 0.10 for Class 1, 2, 3 and 4, respectively. This means that the second machine learning model would predict the concentration corresponding to class 2, with a probability of 0.64. This statistical probability may be displayed to the user; for example, as 64% certainty. In some cases, such probabilities may be adjusted based on other information (for example, SNR).

Figure 5:
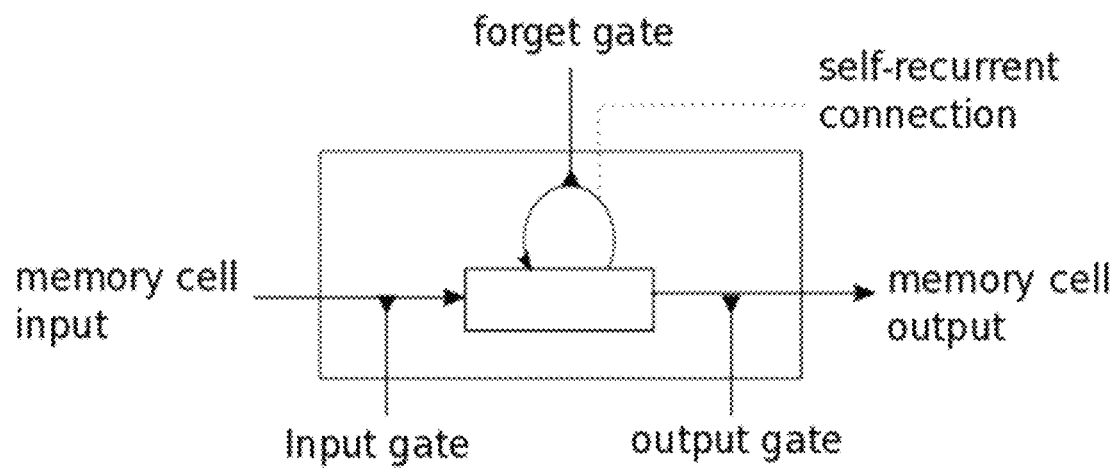
FIG. 5 is a diagrammatic representation of a memory cell.

In an example using the Long Short Term Memory (LSTM) neural network, the LSTM neural network comprises at least three layers of cells. The first layer is an input layer, which accepts the input data. The second (and perhaps additional) layer is a hidden layer, which is composed of memory cells (see FIG. 5). The final layer is output layer, which generates the output value based on the hidden layer using Logistic Regression.

Each memory cell, as illustrated, comprises four main elements: an input gate, a neuron with a self-recurrent connection (a connection to itself), a forget gate and an output gate. The self-recurrent connection has a weight of 1.0 and ensures that, barring any outside interference, the state of a memory cell can remain constant from one time step to another. The gates serve to modulate the interactions between the memory cell itself and its environment. The input gate permits or prevents an incoming signal to alter the state of the memory cell. On the other hand, the output gate can permit or prevent the state of the memory cell to have an effect on other neurons. Finally, the forget gate can modulate the memory cell's self-recurrent connection, permitting the cell to remember or forget its previous state, as needed.

The equations below describe how a layer of memory cells is updated at every time step t. In these equations: $x_t$ is the input array to the memory cell layer at time t. In our application, this is the blood flow signal at all ROIs $$\bar{x}_t = [x_{1t} x_{2t} \ldots x_{nt}]$$

$W_i$, $W_f$, $W_c$, $W_o$, $U_i$, $U_f$, $U_c$, $U_o$ and $V_o$ are weight matrices; and $b_i$, $b_f$, $b_c$ and $b_o$ are bias vectors First, we compute the values for $i_t$, the input gate, and $\tilde{c}_t$ the candidate value for the states of the memory cells at time t:

$$i_t = \sigma(W_i x_t + U_i h_{t-1} + b_i)$$

$$\tilde{C}_t = \tan h(W_c x_t + U_c h_{t-1} + b_c)$$

Second, we compute the value for $f_t$, the activation of the memory cells' forget gates at time t:

$$f_t = \sigma(W_f x_t + U_f h_{t-1} + b_f)$$

Given the value of the input gate activation $i_t$, the forget gate activation $f_t$ and the candidate state value $\tilde{C}_t$, we can compute $C_t$ the memory cells' new state at time t:

$$C_t = i_t * \tilde{C}_t + f_t * C_{t-1}$$

With the new state of the memory cells, we can compute the value of their output gates and, subsequently, their outputs:

$$o_t = \sigma(W_o x_t + U_o h_{t-1} + V_o C_t + b_o)$$

$$h_t = o_t * \tan h(C_t)$$

Based on the model of memory cells, for the blood flow distribution at each time step, we can calculate the output from memory cells. Thus, from an input sequence $x_0$, $x_1$, $x_2$, ..., $x_n$, the memory cells in the LSTM layer will produce a representation sequence $h_0$, $h_1$, $h_2$, ..., $h_n$.

The goal is to classify the sequence into different conditions. The Logistic Regression output layer generates the probability of each condition based on the representation sequence from the LSTM hidden layer. The vector of the probabilities at time step t can be calculated by:

$$p_t = \text{softmax}(W_{output} h_t + b_{output})$$

where $W_{output}$ is the weight matrix from the hidden layer to the output layer, and $b_{output}$ is the bias vector of the output layer. The condition with the maximum accumulated probability will be the predicted condition of this sequence.

In some cases, the blood biomarkers quantification approach, used by the quantification module 112 on the HC change data from the TOI module 110, can utilize adaptive weighting of multiple regions-of-interest (ROIs); and uses minimizing 'noise' criteria to control the weights.

The blood flow localized volume concentrations data captured by the TOI module 110, as described herein, of a human subject's face, as either 'live' or previously recorded, is used as the source data for estimating the quantity of blood biomarkers. The blood flow data signal is specified by the interpretation of the HC changes. As an example, the TOI module 110 can monitor stationary HC changes contained by a selected ROI over time, by observing (or graphing) the resulting temporal profile (for example, shape) of the selected ROI HC intensity values over time. In some cases, the TOI module 110 can monitor more complex migrating HC changes across multiple ROIs by observing (or graphing) the spatial dispersion (HC distribution between ROIs) as it evolves over time.

Figure 7:
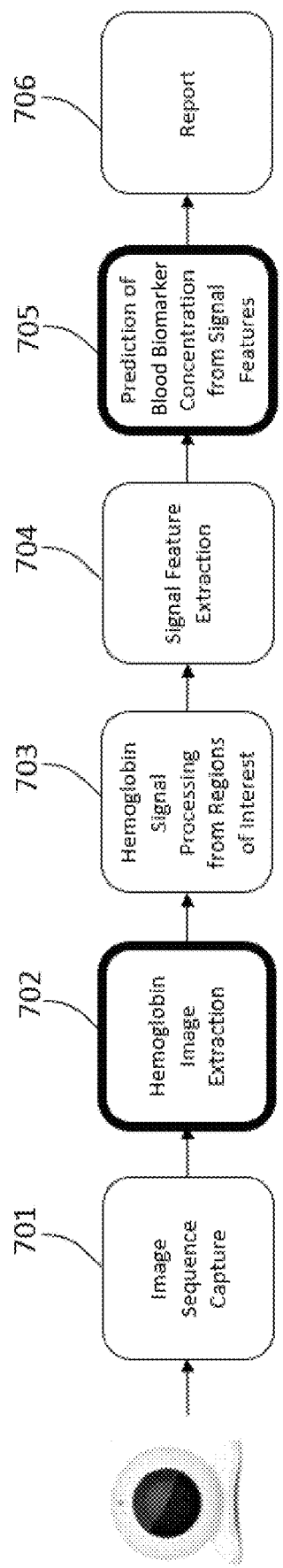
FIG. 7 is an example flowchart illustrating an example of the embodiment of FIG. 1.
Figure 14:
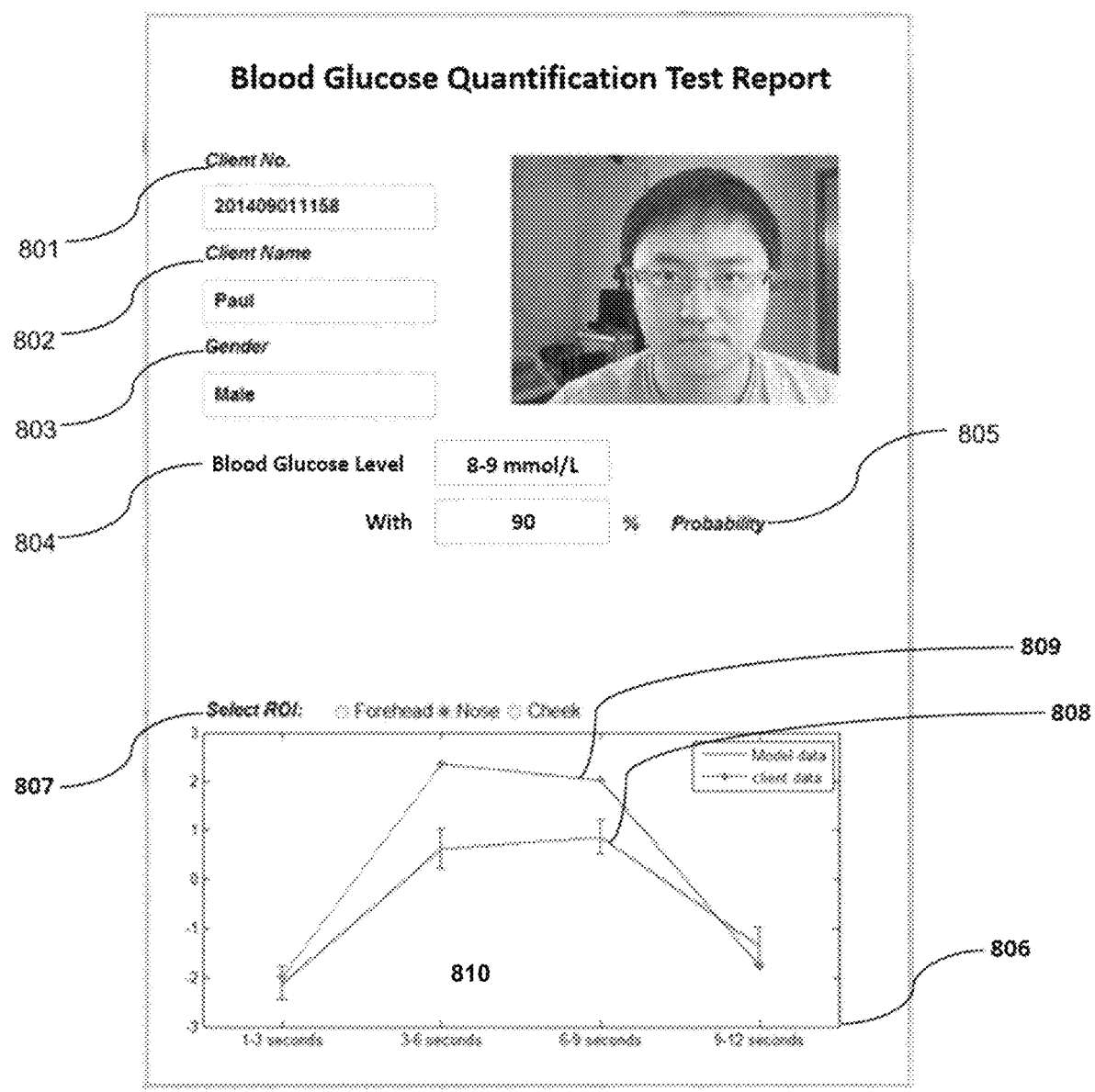
FIG. 14 illustrates an exemplary report illustrating output for quantifying blood biomarkers according to the system of FIG. 1.

Turning to FIG. 7, there is shown a flowchart illustrating an example implementation of the system 100. The example illustrates fully automating transdermal optical imaging for blood content quantification. The system performs captures an image sequence 701 to register the input of a video sequence captured of a subject with an unknown concentration of blood biomarkers, hemoglobin image extraction 702, processes signal from specific regions of interest 703, extracts features from this signal 704, predicts blood biomarkers concentrations from signal features using the second machine learning model 705, and generates a report of the prediction results 708 (for example, as shown in FIG. 14).

Figure 8:
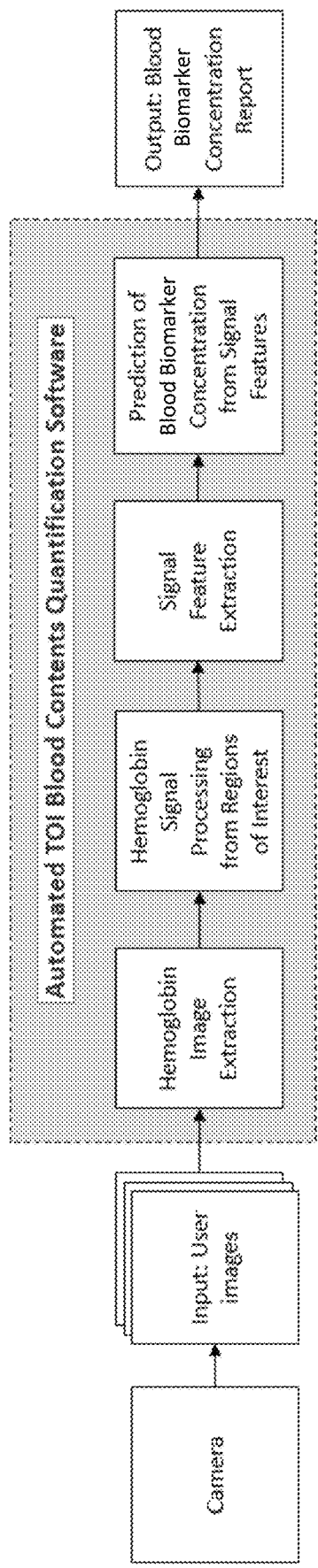
FIG. 8 is another example flowchart illustrating an example of the embodiment of FIG. 1.

Turning to FIG. 8, there is shown a flowchart illustrating another example implementation of the system 100. This example also illustrates fully automating transdermal optical imaging for blood content quantification.

Figure 2:
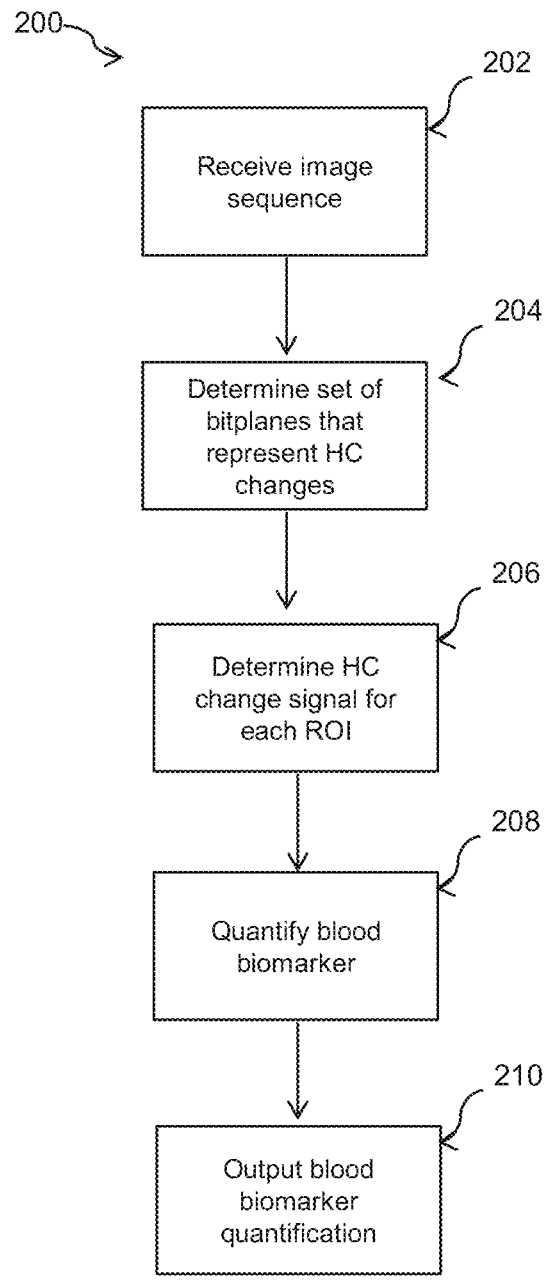
FIG. 2 is a flowchart for a method for camera-based quantification of blood biomarkers, according to an embodiment.

Turning to FIG. 2, a flowchart for a method for camera-based heart rate tracking 200 is shown.

At block 202, the image processing unit 104 receives a sequence of video images from the camera 105 of light re-emitted from the skin of a subject.

The TOI module 110 extracts facial blood flow from the sequence of images using transdermal optical imaging, as described herein. At block 204, the TOI module 110 determines a set of bitplanes in the captured image sequence for each ROI that represent HC changes of the human individual using a trained first machine learning model. The first machine learning model is trained with a hemoglobin concentration (HC) changes training set. The HC changes training set trained using bitplanes from previously captured image sequences of other subjects as input and received cardiovascular data as ground truth data. At block 206, the TOI module 110 determines an HC change signal for each of the ROIs based on changes in the set of determined bitplanes. In this way, the determination by the TOI module 110 can include dynamic changes of localized hemoglobin volume concentrations over time.

At block 208, the HC change signals are passed to a trained second machine learning model by the quantification module 112 for quantification of blood biomarkers. The trained second machine learning module is trained using a blood biomarkers training data set from previously determined HC change signals from other subjects as input and received blood panels as ground truth data.

At block 210, the quantification of blood biomarkers is outputted by the output module 114.

The present inventors conducted example experiments to illustrate the effectiveness of the present embodiments. In the example experiments, the system 100 was used to quantify the blood biomarkers comprising glucose quantities.

Figure 9:
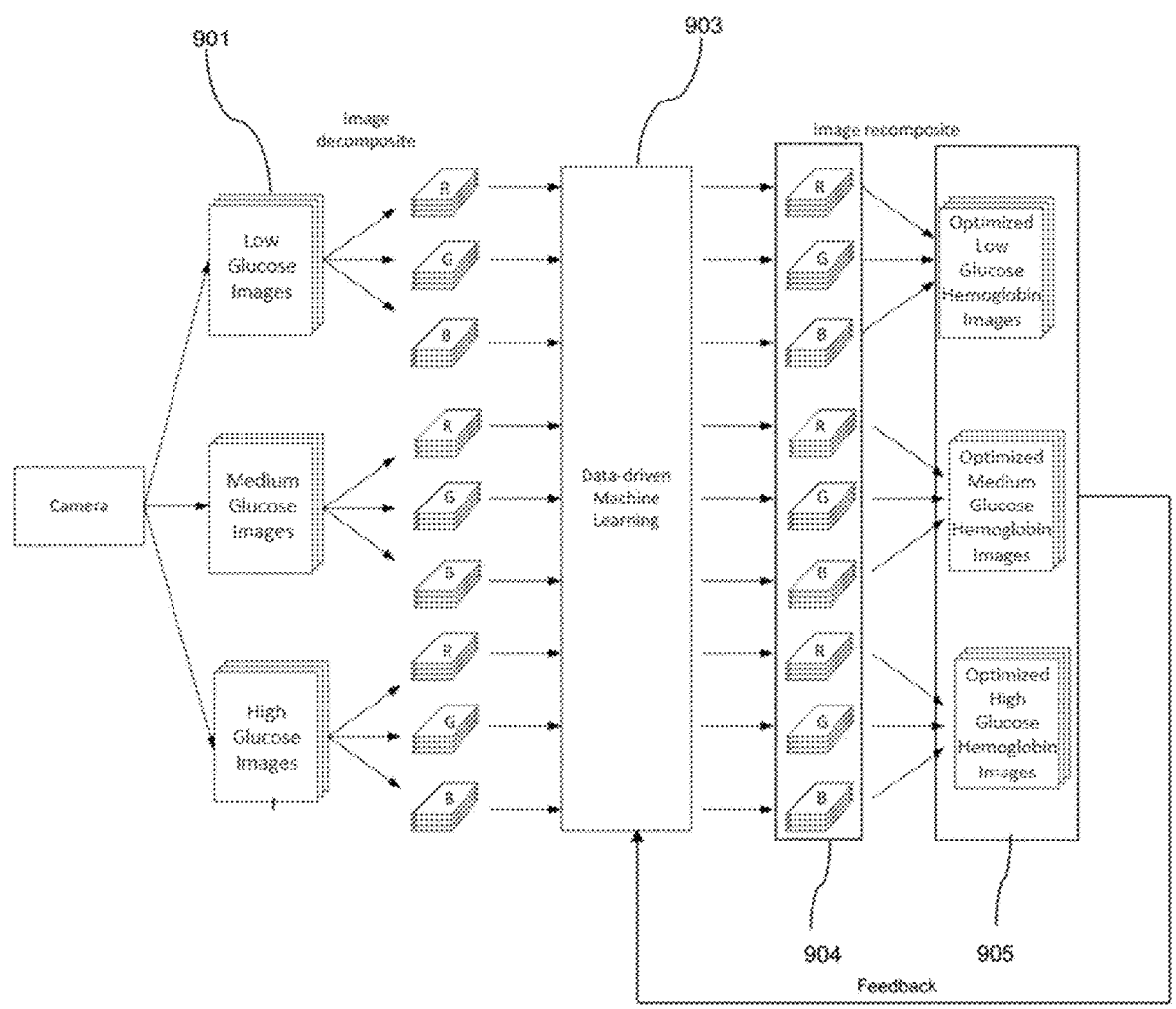
FIG. 9 illustrates application of a portion of the system of FIG. 1 for determining transdermal optical imaging for example experiments.

FIG. 9 illustrates application of a portion of the system 100 for determining transdermal optical imaging using the TOI module 110 for determining blood glucose levels in the example experiments. In this example, using filtered signals from the ROIs of two or more than two concentrations of blood biomarkers 901, the first machine learning model 903 is employed to systematically identify bitplanes 904 that will significantly increase the signal differentiation between the different concentrations of blood biomarkers and bitplanes that will contribute nothing or decrease the signal differentiation between different concentrations of blood biomarkers. After discarding the latter, the remaining bitplane images 905 that optimally, or approximately optimally, differentiate the concentrations of blood biomarkers of interest are obtained. To further improve SNR, the result can be fed back to the machine learning 903 process repeatedly until the SNR reaches an optimal asymptote.

Raw images captured by the camera generally contain information from all bitplanes, but many of these bitplanes can contain information that is not related to HC; for example, information related to light, skin tone, and the like. By extension, such bitplanes may also not carry information related to blood biomarkers. FIG. 9 thus illustrates an example of the present embodiments by which such noise can be removed. This example uses the first machine learning model to identify bitplanes whose information varies most along with hemoglobin and/or the concentration of other blood biomarkers. These determined bitplanes can be collapsed together to form the basis for the "optimized" RGB images.

In the example of FIG. 9, a blood glucose status of the captured images can be generally known due to the ground truth blood panels received at, or around, the time that the images were captured. In this way, "fluctuations" of values in at least some of the bitplanes can be associated by the system 100 with blood glucose fluctuations. In the example of FIG. 9, the blood glucose fluctuations can be categorized into three categories; high, medium, and low. In other cases, blood biomarkers can be categorized in any suitable manner. In other cases, the blood biomarkers can be predicted as a value without categorization.

Figure 10:
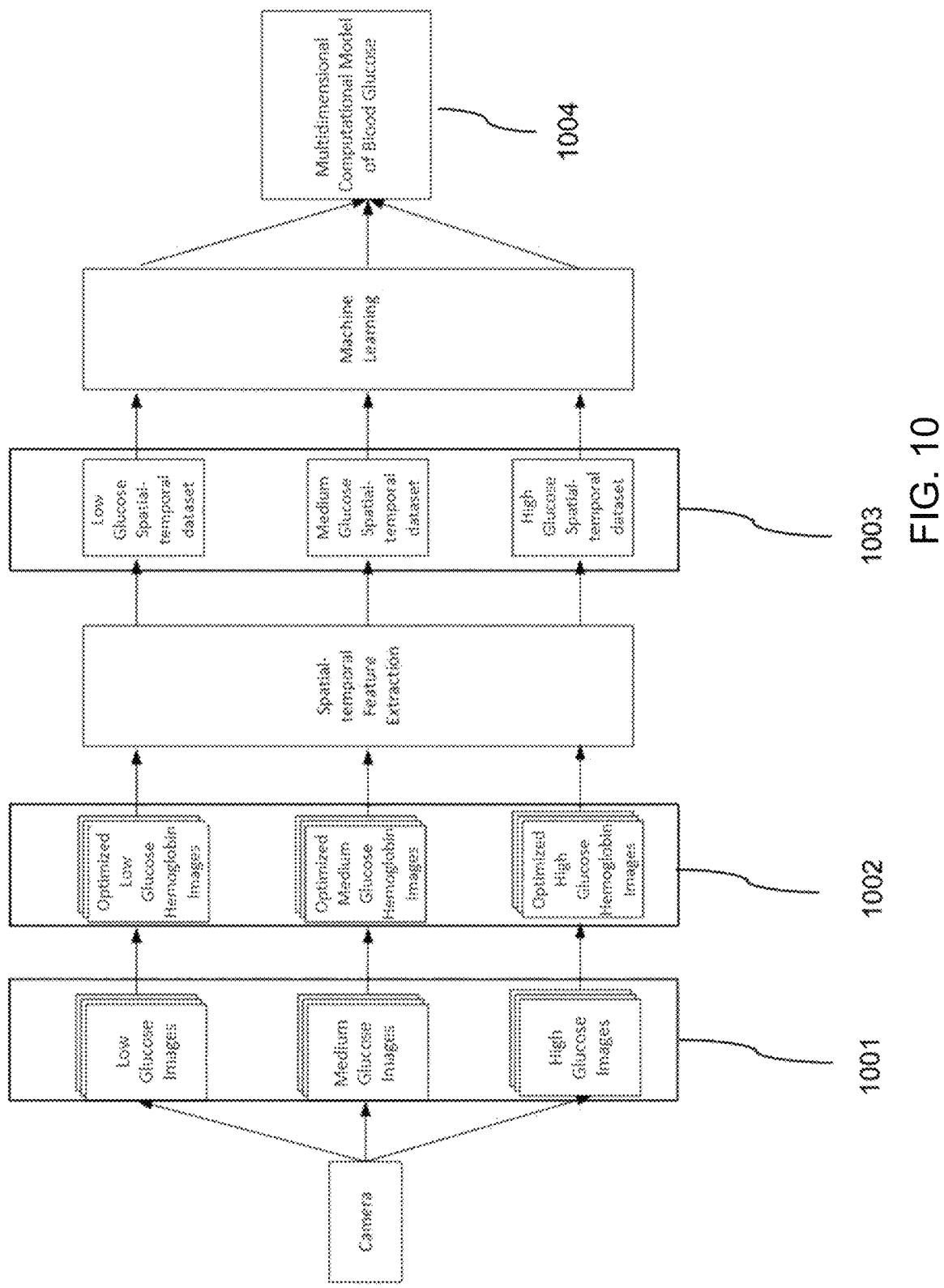
FIG. 10 illustrates application of the system of FIG. 1 for quantifying of blood glucose in the example experiments, using the determinations of FIG. 9.

FIG. 10 illustrates application of the system 100 for quantifying of blood glucose in the example experiments, using the determinations of FIG. 9. In this example, to build the second machine learning model, a second set of training subjects (preferably, a multi-ethnic group of training subjects with different skin types) is used, and image sequences 1001 are obtained from such subjects in conjunction with blood panel results. The image filter 106 is applied to the image sequences 1001 to generate high HC SNR image sequences. Using this new training set of subject HC content data 1003 derived from the bitplane filtered images 1002, the second machine learning model is used to build computational models for concentrations of various blood biomarkers 1003. In some cases, the second machine learning model again uses a portion of data received from images captured of a subject (e.g., 70%, 80%, 90% of the subject data) and uses the remaining subject data to test and/or validate the model. This second machine learning model comprises separate multidimensional (spatial and temporal) computational models for each blood biomarker using trained concentrations of the blood biomarkers 1004; in this case, a model for blood glucose quantities. In further cases, the second machine learning model can comprise computational models that comprise predictions for more than one blood biomarker.

Figure 11:
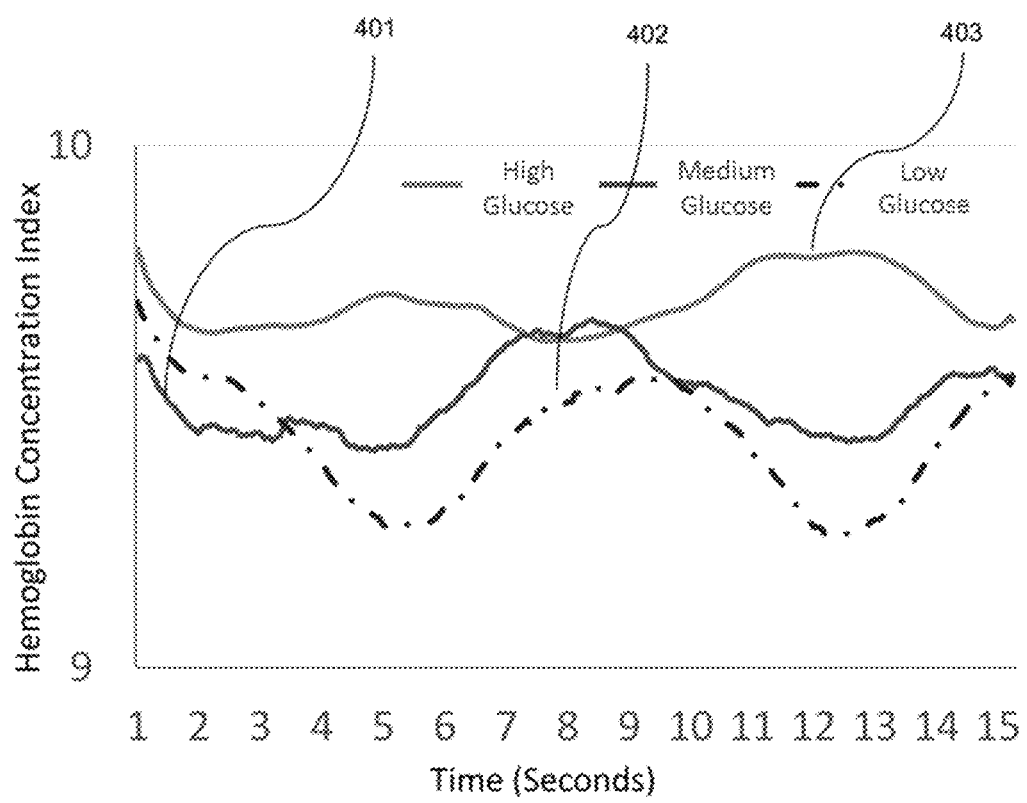
FIG. 11 is a plot of the example experiments of FIG. 9 illustrating differences in hemoglobin distribution for a forehead of a subject, differences in hemoglobin distribution for the nose and cheek of a subject may be seen in FIG. 12 and FIG. 13 respectively.
Figure 12:
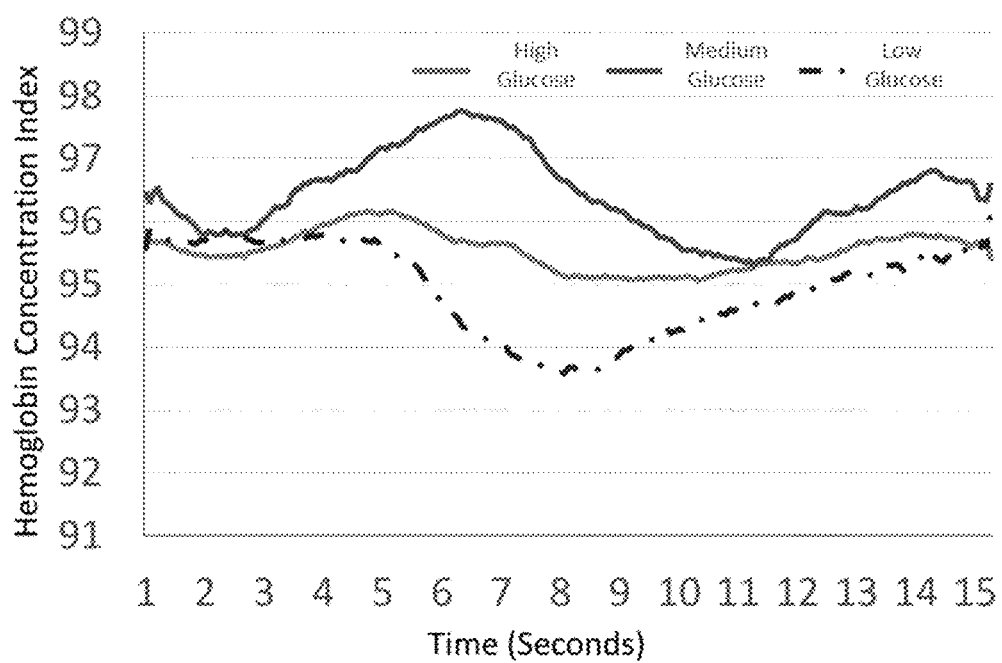
FIG. 12 is a plot of the example experiments of FIG. 9 illustrating differences in hemoglobin distribution for a nose of the subject.
Figure 13:
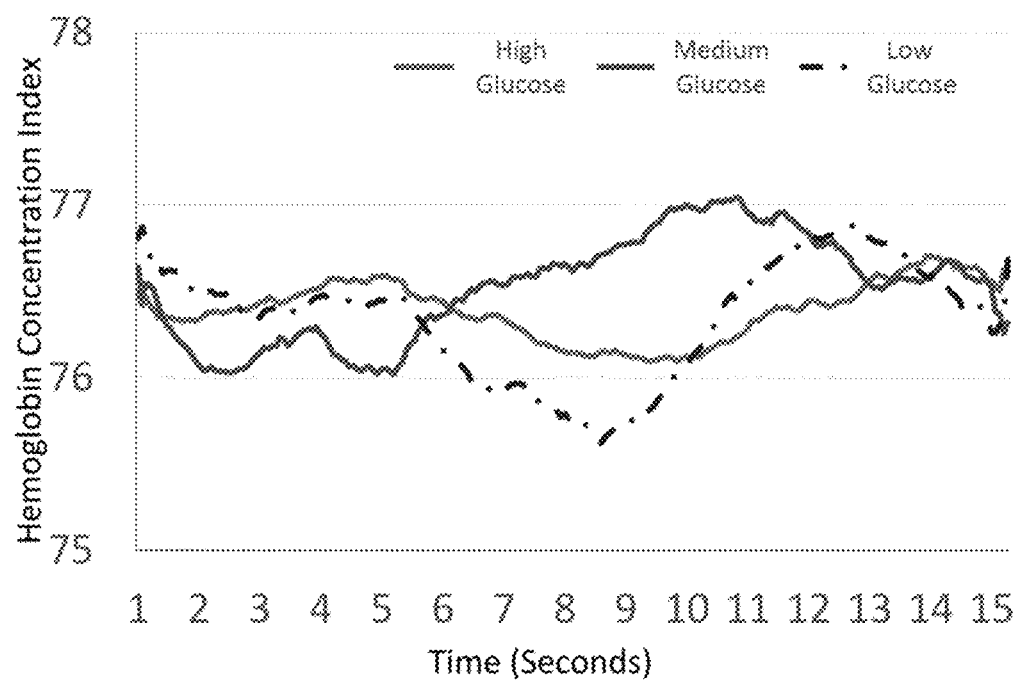
FIG. 13 is a plot of the example experiments of FIG. 9 illustrating differences in hemoglobin distribution for a cheek of the subject.

FIG. 11 is a plot of the example experiments illustrating differences in hemoglobin distribution for the forehead of a subject. Transdermal images, determined by the TOI module 110, show a marked difference in hemoglobin distribution between medium 401, low 402 and high 403 reference blood glucose concentration. Similarly, differences in hemoglobin distribution for the nose and cheek of a subject may be seen in FIG. 12 and FIG. 13 respectively.

FIG. 14 illustrates an exemplary report illustrating the output of the output module 114 for quantifying blood biomarkers. The system 100 may attribute a unique client number 801 to a given subject's first name 802 and gender 803. The concentration of the blood biomarker 804 is identified with a given probability 805. In an embodiment, the report may include a graph 810 comparing concentration of the blood biomarker 806 based on a given combination of ROIs 807 as compared to model data 808, over time 809.

In a particular case, the output can be a probability, as level of certainty (expressed as a percentage), that the subject's blood flow belongs to a given concentration class within a multi-classification approach. In some cases, level of certainty (as a proportion from 0 to 1) for each class of each respective blood biomarkers in the multi-classification approach can be determined using a Softmax function, as described herein. The desired proportion can be multiplied by 100 to get a percentage.

In further embodiments, the camera can be directed to the skin of different body parts, such as for example the wrist or neck. From these body areas, the system may also extract dynamic hemoglobin changes to determine blood flow, and thus acquire concentrations of various blood biomarkers as described herein. In some cases, optical sensors pointing, or directly attached to the skin of any body parts such as for example the wrist or forehead, in the form of a wrist watch, wrist band, hand band, clothing, footwear, glasses or steering wheel may be used. From these body areas, the system may also extract blood flow data for heart rate determinations.

In example applications, the present embodiments may be used to improve certain aspects of the health care industry. End users may use the system to go make routine health self-assessments that are actionable by the end user (e.g., blood glucose monitoring for adjusting diet or insulin dosing; unfavorable cholesterol to suggest dietary changes) or require more in-depth follow-up by a medical professional (e.g., low red blood cell count could suggest the user should be evaluated for anemia). Medical doctors, dentists, psychologists, psychiatrists, and the like, may use the present embodiments to monitor disease, mineral content, pharmaceutical drug effectiveness, organ function, and the like.

In an example application, the present embodiments may be used as part of customs or public health screening processes; such as being used to screen individuals boarding transportation (e.g., aircraft) or other public places for communicable diseases or impending need for urgent medical care, or to conduct a preliminary scan for disease on individuals entering the country from overseas.

In another example application, the present embodiments may be used for monitoring a diet or fitness regimen. For instance, monitoring creatinine levels could be used to indicate muscle anabolism versus catabolism. Red blood cell count or hemoglobin concentration could be used to indicate oxygen carrying capacity.

In another example application, the present embodiments may be used as a tool in medical research and exercise science. For example, the system could screen research participants for health abnormalities or monitor the response to experimental treatment.

It will be appreciated that while the present embodiments described a system and method for quantification of blood biomarkers, the aspects of the embodiments described herein could be applied to detection of any other condition for which blood concentration flow is an indicator.

Other applications may become apparent.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A method for determination of a concentration of one or more blood biomarkers of a human subject, the method comprising:
   receiving a captured image sequence of light re-emitted from the skin of the human subject;
   determining, using a first machine learning model trained with a hemoglobin concentration (HC) changes training set, bit values from a set of bitplanes in the captured image sequence that represent the HC changes of the subject, the set of bitplanes being those that are determined to approximately maximize a signal-to-noise ratio (SNR), the HC changes training set comprising bit values from each bitplane of images captured from a set of subjects for which HC changes are known;
   determining, using a second machine learning model trained using a blood biomarkers training set, concentration of one or more blood biomarkers, the blood biomarkers training set comprising previously determined HC change signals from other subjects and one or more blood panels from those subjects as ground truth data; and
   outputting the determined concentration of one or more blood biomarkers.

2. The method of claim 1, wherein determining the bit values comprises determining a bit values for each of a plurality of predetermined regions of interest (ROIs) of the human subject captured by the images based on the HC changes.

3. The method of claim 2, wherein the ROIs are non-overlapping.

4. The method of claim 1, wherein the concentration of one or more blood biomarkers determined using the second machine learning model comprises an estimated statistical probability that a blood concentration of each of the one or more blood biomarkers belongs to a particular concentration range.

5. The method of claim 4, wherein the concentration ranges are associated with clinically significant concentration classes.

6. The method of claim 1, wherein the captured image sequence comprises images captured in a moving time window, and wherein the determined concentration of one or more blood biomarkers is outputted for each moving time window.

7. The method of claim 1, wherein each of the one or more blood biomarkers comprise one of blood glucose concentration, fasting blood glucose, hemoglobin A1c, high density lipoprotein, low density lipoprotein, triglycerides, neutrophils, basophils, creatinine, uric acid, red blood cells, hemoglobin, platelets, sediment, and albumin.

8. The method of claim 1, wherein determining a set of bitplanes that maximize SNR comprises:
   performing pixelwise image subtraction and addition of bitplane vectors to maximize signal differences in all ROIs over a predetermined time period;
   identifying bit values from bitplanes that increase the signal differentiation and bit values from bitplanes that decrease the signal differentiation or do not contribute to signal differentiation; and
   discarding the bit values from the bitplanes that decrease the signal differentiation or do not contribute to signal differentiation.

9. The method of claim 1, wherein the second machine learning model comprises a Long Short Term Memory (LSTM) artificial neural network or Gaussian Process Inference Networks (GPNet).

10. A system for determination of a concentration of one or more blood biomarkers of a human subject, the system comprising one or more processors and a data storage device, the one or more processors configured to execute:
    a TOI module to receive a captured image sequence of light re-emitted from the skin of the human subject and to determine, using a first machine learning model trained with a hemoglobin concentration (HC) changes training set, bit values from a set of bitplanes in the captured image sequence that represent the HC changes of the subject, the set of bitplanes being those that are determined to approximately maximize a signal-to-noise ratio (SNR), the HC changes training set comprising bit values from each bitplane of images captured from a set of subjects for which HC changes are known;
    a quantification module to determine, using a second machine learning model trained using a blood biomarkers training set, concentration of one or more blood biomarkers, the blood biomarkers training set comprising previously determined HC change signals from other subjects and one or more blood panels from those subjects as ground truth data; and
    an output module to output the determined concentration of one or more blood biomarkers.

11. The system of claim 10, wherein determining the bit values comprises determining a bit values for each of a plurality of predetermined regions of interest (ROIs) of the human subject captured by the images based on the HC changes.

12. The system of claim 11, wherein the ROIs are non-overlapping.

13. The system of claim 10, wherein the concentration of one or more blood biomarkers determined using the second machine learning model comprises an estimated statistical probability that a blood concentration of each of the one or more blood biomarkers belongs to a particular concentration range.

14. The system of claim 13, wherein the concentration ranges are associated with clinically significant concentration classes.

15. The system of claim 10, wherein the captured image sequence comprises images captured in a moving time window, and wherein the determined concentration of one or more blood biomarkers is outputted for each moving time window.

16. The system of claim 10, wherein each of the one or more blood biomarkers comprise one of blood glucose concentration, fasting blood glucose, hemoglobin A1c, high density lipoprotein, low density lipoprotein, triglycerides, neutrophils, basophils, creatinine, uric acid, red blood cells, hemoglobin, platelets, sediment, and albumin.

17. The system of claim 10, wherein determining a set of bitplanes that maximize SNR comprises:
- performing pixelwise image subtraction and addition of bitplane vectors to maximize signal differences in all ROIs over a predetermined time period;
- identifying bit values from bitplanes that increase the signal differentiation and bit values from bitplanes that decrease the signal differentiation or do not contribute to signal differentiation; and
- discarding the bit values from the bitplanes that decrease the signal differentiation or do not contribute to signal differentiation.

18. The system of claim 10, wherein the second machine learning model comprises a Long Short Term Memory (LSTM) artificial neural network or Gaussian Process Inference Networks (GPNet).

\* \* \* \* \*